United States Patent
Hayashi et al.

(10) Patent No.: US 10,022,459 B2
(45) Date of Patent: Jul. 17, 2018

(54) MEDICAL TISSUE-MARKER AND MANUFACTURING METHOD FOR THE SAME

(75) Inventors: Hideki Hayashi, Chiba (JP); Hirosuke Hatayama, Chiba (JP); Masanori Fujinami, Chiba (JP); Taro Toyota, Chiba (JP)

(73) Assignee: NATIONAL UNIVERSITY CORPORATION CHIBA UNIVERSITY, Chiba-Shi, Chiba (JP)

( * ) Notice: Subject to any disclaimer, the term of this patent is extended or adjusted under 35 U.S.C. 154(b) by 690 days.

(21) Appl. No.: 14/126,034

(22) PCT Filed: May 31, 2012

(86) PCT No.: PCT/JP2012/064235
§ 371 (c)(1),
(2), (4) Date: Apr. 14, 2014

(87) PCT Pub. No.: WO2012/173003
PCT Pub. Date: Dec. 20, 2012

(65) Prior Publication Data
US 2014/0219924 A1    Aug. 7, 2014

(30) Foreign Application Priority Data
Jun. 13, 2011  (JP) ................. 2011-130901

(51) Int. Cl.
*A61K 49/00* (2006.01)
*A61K 49/04* (2006.01)

(52) U.S. Cl.
CPC ...... *A61K 49/0034* (2013.01); *A61K 49/0002* (2013.01); *A61K 49/0023* (2013.01); *A61K 49/0084* (2013.01); *A61K 49/0438* (2013.01); *A61K 49/0466* (2013.01)

(58) Field of Classification Search
CPC ............ A61K 49/0023; A61K 49/0438; A61K 49/0466; A61K 49/0002; A61K 49/0084; A61K 49/0034
See application file for complete search history.

(56) References Cited

U.S. PATENT DOCUMENTS 4,917,880 A * 4/1990 Wretlind ............ A61K 49/0461
424/9.4

FOREIGN PATENT DOCUMENTS

| JP | 2005-263647 | 9/2005 |
| JP | 2010-266295 | 11/2010 |

OTHER PUBLICATIONS

Translation of Toyoda Taro JP 2010-266295.*
Haruhiro Ankoh, "*Lecithin Haigo lipidol emulsion o Mochiita Kandochu Kagaku Sokusen Ryoho no Kisoteki Kenkyu*", Journal of Tokyo Womens Medical University, 1990, vol. 60, No. 12, pp. 999-1010.
International Search Report of PCT/JP2012/064235 (1 page).

* cited by examiner

*Primary Examiner* — Michael G Hartley
*Assistant Examiner* — Nabila G Ebrahim
(74) *Attorney, Agent, or Firm* — Flynn, Thiel, Boutell & Tanis, P.C.

(57) ABSTRACT

A medical tissue-marker which enables the identification of a location even from the outside of an organ, can remain topical over a long period, and enables the easy identification of a marked location within the whole organ; also a manufacturing method for the medical tissue-marker. The medical tissue-marker includes a vesicle formed by the synthesis of a phospholipid and a near infrared fluorescent dye, and an emulsion formed by the synthesis of the phospholipid and an X-ray contrast medium, and has agglomerated clusters wherein the vesicle and the emulsion are contained in a hydrophilic solvent and a plurality of capsules are formed by use of an emulsifier.

2 Claims, 25 Drawing Sheets

MEDICAL TISSUE-MARKER AND MANUFACTURING METHOD FOR THE SAME

TECHNICAL FIELD

The present invention relates to a medical tissue-marker and a manufacturing method for the same.

BACKGROUND ART

Recently, a surgical operation using an endoscope has been developed and employed in a method for diagnosis and a medical treatment. In a surgical operation, a tissue-marker is extremely useful. A tissue-marker makes a mark on region to be diagnosed or medically treated. A region for diagnosis and a medical treatment can be easily identified by making a mark.

Techniques for a well-known tissue-marker such as indocyanine green are disclosed, for example, in non-patent literatures 1 to 6, and patent literatures 1 and 2 (hereinafter, referred to as "literatures"). In literatures described below, it is disclosed that a tissue-marker fabricated by combining indocyanine green and gelatin is used, and absorption for a visible region is observed by an endoscope camera.

A technique using X-ray contrast mediums such as iodized poppy oil ethyl ester as a tissue-marker is disclosed in non-patent literature 7 described below. In the literatures described below, it is disclosed that a tissue-marker fabricated by combining the iodized poppy oil ethyl ester and a phospholipid is more stable than a tissue-marker in which no phospholipid is used.

Furthermore, in the patent literature 3, a vesicle formed by combining a phospholipid and a near-infrared fluorescent dye is incorporated into a hydrophilic solvent to prepare a medical tissue-marker having a vesicle cluster where a plurality of capsules are formed and aggregated by an emulsifier.

Non-patent literature 1: edited and written by Kusano Mitsuo, All about ICG fluorescent Navigation Surgery, Intermedia, 2008

Non-patent literature 2: S. Yoneya et al, Investigative Ophthalmology and Visual Science 1998; 39: 1286-1290

Non-patent literature 3: S. Ito et al, Endoscopy 2001; 33: 849-853

Non-patent literature 4: R. Ashida et al, Endoscopy 2006; 38: 190-192

Non-patent literature 5: S. Taoka et al, Digestive Endoscopy 1999; 11: 321-326

Non-patent literature 6: J. V. Frangioni, Current Opinion in Chemical Biology 2003; 7: 626-634

Non-patent literature 7: Ahkoh Seihiro, basic research for hepatic artery chemoembolotherapy using lipiodol emulsion mixed with lecithin, Tokyo Medical Women's College magazine, 1990; 60: 999-1010

Patent literature 1: Japanese Unexamined Patent Application Publication No. 2007-262062

Patent literature 2: Japanese Unexamined Patent Application Publication No. 2008-69107

Patent literature 3: Japanese Unexamined Patent Application Publication No. 2010-266295

DESCRIPTION OF THE INVENTION

Problems to be Solved by the Invention

Techniques disclosed in non-patent literatures 1 to 6, and patent literatures 1 and 2 are useful for roughly catching a marking position for tissue. However, it is not easy to use an identification that precisely determines a minimum range of tissue to be excised. Specifically, in techniques described above, a tissue inside in an organ and a marker for marking the tissue can be directly observed by an endoscope. However, it is difficult to confirm a marking position inside in an organ by observation from the outside of an organ in which visible light cannot be transmitted, and to excise a target lesion with minimum margins. Furthermore, when ICG is simply mixed with gelatin, identifying a marking position is difficult because diffusion occurs through tissues of a body in an early stage.

These problems mean that there is room for functional improvement in a marker. It is difficult to find ordinary markers placed inside in an organ from the outside of the organ. A marker with fluorescence of a near-infrared light wavelength range can be detected from outside of the organ since near-infrared light can be transmitted through biological tissues. However, such a marker immediately diffuses after administration and a marking point becomes blurred. As a result, an organ with a target lesion is unnecessarily widened to be excised and a burden on a patient is increased.

These problems described above can be solved by a technique disclosed in patent literature 3. However, it is not easy to catch a marking position within an entire organ. For example, if a marking position is easily detected from the outside of an organ by X-ray computed tomography (CT) and an endoscope, it is expected that the information of the marking position can be utilized for a simulation before surgery as well as navigation during surgery.

In the technique disclosed in the non-patent literature 7, iodized poppy oil ethyl ester having a poor water-solubility is protected by a phospholipid. Thus, there are merits that the dispersibility of the iodized poppy oil ethyl ester in water and retentivity in a body are enhanced. However, since the dispersion liquid has a high fluidity, when an organ is marked, the fixation thereof is low and it leaks out of the marking point.

Thus, in order to solve the above mentioned problem, it is an object of the present invention to provide a medical tissue-marker and a manufacturing method for the same in which it is possible to identify a position from the outside of an organ, it is easy to be locally stable for a long period, and it is easy to make a marking position within an entire organ.

Means for Solving the Problems

A medical tissue-marker according to one aspect of the present invention to solve the above problem comprises a vesicle formed by combining a phospholipid and a near-infrared fluorescent dye, an emulsion formed by combining the phospholipid and an X-ray contrast medium, the vesicle and the emulsion being incorporated into a hydrophilic solvent, and a cluster in which a plurality of capsules are formed and aggregated by an emulsifier.

A method for manufacturing a medical tissue-marker according to another aspect of the present invention comprises adding a near-infrared fluorescent dye, an X-ray contrast medium and a phospholipid into a first hydrophilic solvent and stirring the first hydrophilic solvent, adding the first hydrophilic solvent and an emulsifier into a hydrophobic solvent to form a suspension, and performing centrifugation on the suspension and a second hydrophilic solvent.

Effects of the Invention

Thus, according to the present invention, a medical tissue-marker and a manufacturing method for the same can be provided. It is possible to identify a position even on the outside of an organ and to be stable for a long period, and it is easy to make a marking position within an entire organ.

BEST MODE FOR CARRYING OUT THE PRESENT INVENTION

Hereinafter, the embodiments of the present invention are described with reference to the drawings. However, the present invention can be accomplished with different embodiments and is not limited to the embodiments and examples described below.

Embodiment 1

(A Medical Tissue-Marker)

Figure 1:
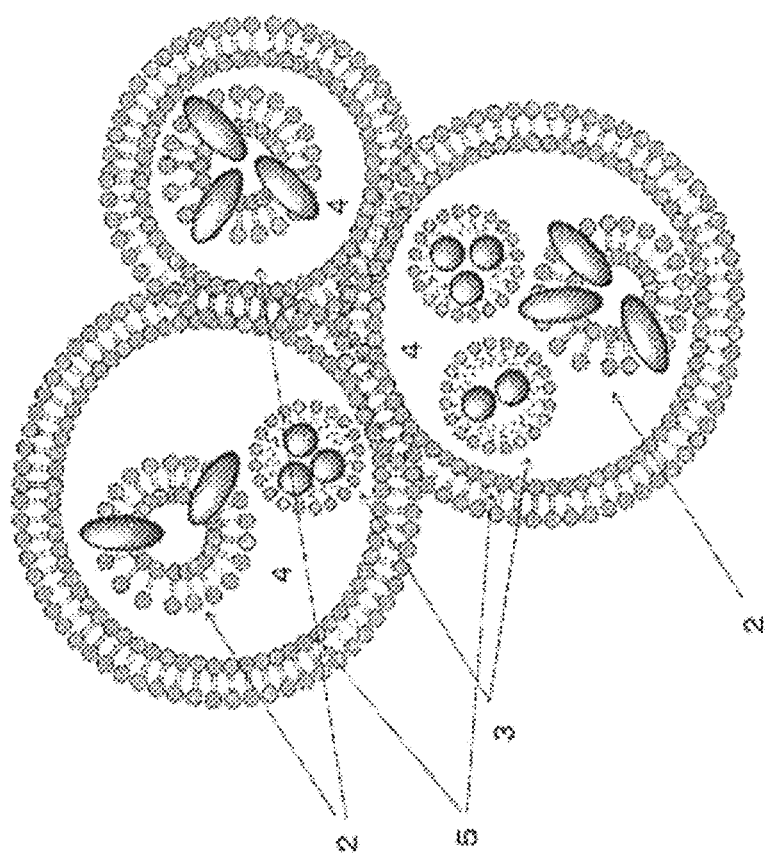
FIG. 1 shows a schematic view for clusters according to one embodiment.
Figure 2:
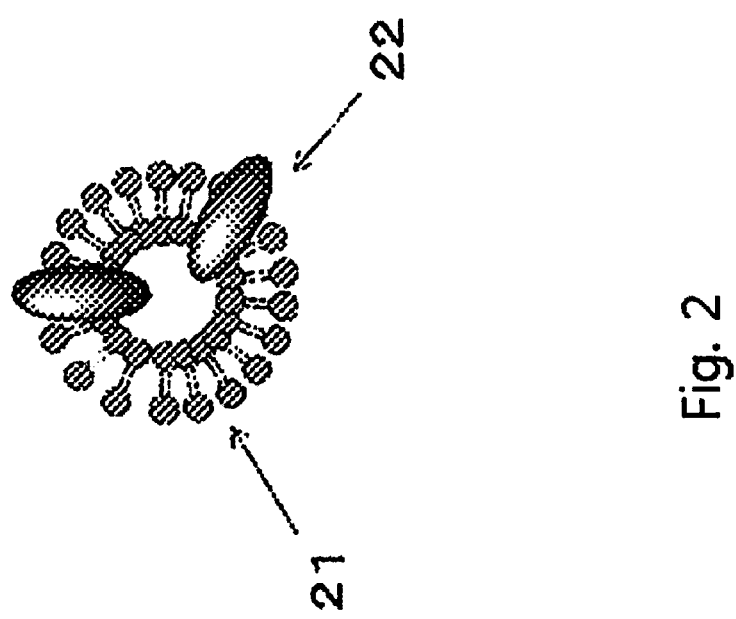
FIG. 2 shows a schematic view for a vesicle according to one embodiment.
Figure 3:
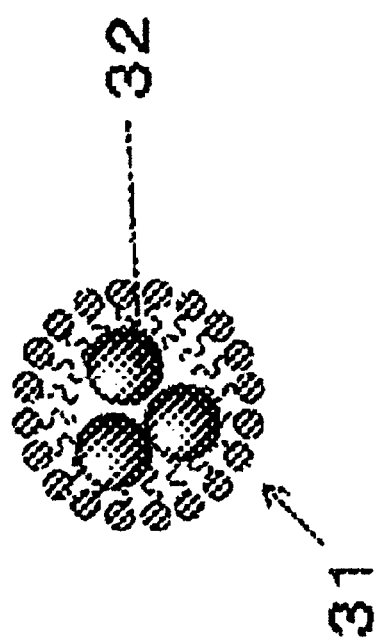
FIG. 3 shows a schematic view for an emulsion according to one embodiment.

A medical tissue-marker according to the present embodiment 1 comprises a vesicle formed by combining a phospholipid and a near-infrared fluorescent dye, an emulsion formed by combining the phospholipid and an X-ray contrast medium, the emulsion being incorporated into a hydrophilic solvent, and has clusters in which a plurality of capsules are formed and aggregated by an emulsifier (hereinafter, referred to as "clusters"). FIG. 1 shows a schematic view of the clusters 1 in a medical tissue-marker according to the present embodiment 1. FIG. 2 shows a schematic view of a vesicle 2 contained in the clusters 1, and FIG. 3 shows a schematic view of an emulsion 3 contained in the clusters 1.

As shown in FIG. 2, a vesicle 2 according to the present embodiment 1 is formed by including phospholipids 21 and near-infrared fluorescent dyes 22. Herein, the vesicle 2 means bag-shaped bilayer membranes formed by self-assembled phospholipids due to intermolecular forces. The near-infrared fluorescent dyes 22 are combined with the phospholipids 21 to become components of the vesicle 2. Herein, the "combination" means a state of forming a complex with a vesicle mainly by intermolecular interaction of hydrophobic interaction or means a state of being dissolved in the vesicle 2. By combining the near-infrared fluorescent dyes 22 with the phospholipids 21, the vesicle 2 according to the present embodiment 1 stabilizes the near-infrared fluorescent dyes 22 to stably generate fluorescent light in a near-infrared region.

The phospholipids 21 according to the present embodiment 1 are not limited as long as a vesicle can be formed. Examples thereof may be lecithin, phosphatidylcholine, or mixtures thereof. The lecithin is not limited. However, examples thereof may be egg yolk lecithin, soybean lecithin, or mixtures thereof. From the viewpoint of fluorescence intensity in a body, the phospholipids 21 are preferably egg yolk lecithin.

The phosphatidylcholine is not limited as long as the requirement described above is satisfied. Examples thereof may be 1-palmitoyl-2-oleoyl-3-sn-glycerophosphatidylcholine, 1-stearyl-2-oleoyl-3-sn-glycerophosphatidylcholine, 1-palmitoyl-2-linoleate-3-sn-glycerophosphatidylcholine, 1-stearyl-2-linoleate-3-sn-glycerophosphatidylcholine, 1,2-dilinoleate-3-sn-phosphatidylcholine, 1,2-dipalmitoyl-3-sn-glycerophosphatidylcholine, 1,2-distearyl-3-sn-glycerophosphatidylcholine, 1,2-dilinoleate-3-sn-glycerophosphatidylcholine, or mixtures thereof.

In the present embodiment 1, the near-infrared fluorescent dyes 22 may be indocyanine green, brilliant green, Indigo Carmine or derivatives thereof. The near-infrared fluorescent dyes 22 means a compound in which a portion of the indocyanine green, the brilliant green or the Indigo Carmine is substituted with other functional groups, while maintaining the main structure and function thereof. The indocyanine green, the brilliant green and the Indigo Carmine are expressed by chemical formulae 1, 2, and 3, respectively.

[chemical formula 1]

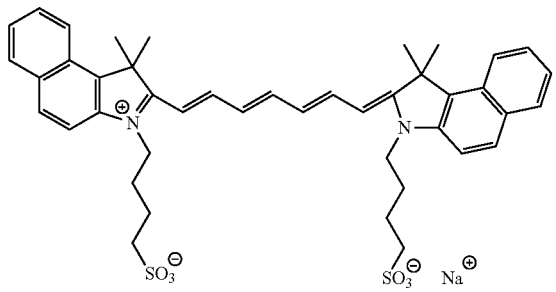

(1)

[chemical formula 2]

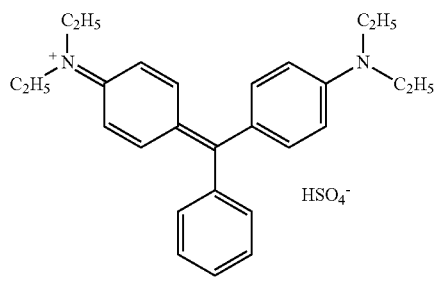

(2)

[chemical formula 3]

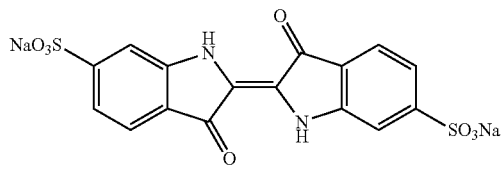

(3)

Size of the vesicle 2 according to the present embodiment 1 is not particularly limited. Generally, the size thereof is preferably 10 nm or more and 100 μm or less, and is more preferably 100 nm or more and 101 μm or less.

In the vesicle 2 according to the present embodiment 1, the amounts of the phospholipids 21 and the near-infrared fluorescent dyes 22 can be adjusted without limitation. For example, when the amount of lecithin of the phospholipids 21 is one, the amount of indocyanine green of the near-infrared fluorescent dyes 22 is preferably $1\times10^{-4}$ or more and $1\times10^{-3}$ or less, and is more preferably $4\times10^{-3}$ or more and $6\times10^{-3}$ or less. Within the range of $1\times10^{-4}$ or more and $1\times10^{-3}$ or less, it is easy to identify a marking position for a tissue in the inside of an organ from the outside of an organ. Within the range of $4\times10^{-3}$ or more and $6\times10^{-3}$ or less, the effect thereof becomes more remarkable.

As shown in FIG. 3, an emulsion 3 according to the present embodiment 1 is formed by including phospholipids 31 and X-ray contrast mediums 32. Herein, the emulsion 3 means a particles-wrapped bimolecular film formed by the phospholipids 31 which is self-assembled due to intermolecular interaction. The X-ray contrast medium 32 mean a component of the emulsion 3 in combination with the phospholipids 31. Herein, the "combination" means a state of forming a complex with the phospholipids 31 mainly by intermolecular interaction of hydrophobic interaction or means a state of being dissolved in the emulsion 3. By combining the X-ray contrast mediums 32 with the phospholipids 31, the emulsion 3 according to the present embodiment 1 stabilizes the X-ray contrast mediums 32 to properly capture an X-ray CT image.

The phospholipids 31 according to the present embodiment 1 are similar to the phospholipids 21 in the vesicle In the present embodiment 1, the X-ray contrast mediums 32 are not limited. Examples thereof preferably are iodized poppy oil ethyl ester and derivatives thereof, iodobenzene and derivatives thereof, and barium salt or mixtures thereof. The iodized poppy oil ethyl ester is a compound obtained by iodization and esterification of a poppy oil fatty acid. Examples of the iodized poppy oil ethyl ester can be expressed by a chemical formula (4). From the viewpoint of the X-ray absorption ratio in an organ, the X-ray mediums 32 are preferably the iodized poppy oil ethyl ester.

[chemical formula 4]

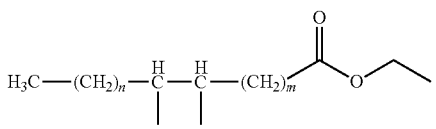

(4)

(wherein, n is an integer of 1 to 10, and m is an integer of 2 to 12.)

The size of the emulsion 3 according to the present embodiment 1 is not particularly limited. Generally, the size thereof is preferably 10 nm or more and 100 μm or less, and is more preferably 100 nm or more and 10 μm or less.

In the emulsion 3 according to the present embodiment 1, the amounts of the phospholipids 31 and the X-ray contrast mediums 32 can be adjusted without limitation. For example, when the amount of lecithin of the phospholipids 31 is one, the amount of the iodized poppy oil ethyl ester of the X-ray contrast medium 32 is preferably $1\times10^{1}$ or more and $1\times10^{3}$ or less, and is more preferably $2\times10^{-1}$ or more and $2\times10^{1}$ or less. Within the range of $1\times10^{-1}$ or more and $1\times10^{3}$ or less, it is possible to sufficiently protect the surface of the emulsion 3 of the iodized poppy oil ethyl ester with a film of the phospholipids 31. Within the range of $2\times10^{-1}$ or more and $2\times10^{1}$ or less, the effect thereof becomes more remarkable.

As shown in FIG. 1, the clusters 1 according to the present embodiment 1 includes a plurality of capsules 5 in which a hydrophilic solvent 4 is incorporated, wherein the plurality of capsules 5 are formed and aggregated by an emulsifier. In the hydrophilic solvent 4, at least any one of the vesicle 2 and the emulsion 3 is incorporated.

The hydrophilic solvent 4 is used for the vesicle 2 and the emulsion 3 being stably incorporated and is not limited as far as the above condition is satisfied. Preferably, an example thereof is water, physiological salt water, phosphate buffer solution, TRIS hydrochloric acid buffer solution, HEPES buffer solution, or mixtures thereof. When a phosphate buffer solution, TRIS hydrochloric acid buffer solution or HEPES buffer solution is used, the pH range of 6.5 or more and 8 or less is preferable.

In order to perform stably for a long period at a marking position of a tissue in a body, an edible thickener is preferably added into the hydrophilic solution 4. Examples thereof are not limited and may be gelatin, agar, fibrinogen, saccharide, or mixtures thereof.

Examples of the gelatin are not limited and may be collagen type I, collagen type II, collagen type III, collagen type V or mixtures thereof.

Examples of the agar are not limited and may be agarose, agaropectin, or mixtures thereof, the agarose and the agaropectin having a molecular weight of from several thousands to several ten thousands.

Examples of the fibrinogen are not limited. For example, fibrinogen having a concentration of from 5 mg/mL to 50 mg/mL as a main ingredient is included, and calcium chloride, prothrombin, or mixtures thereof is also included.

Examples of a saccharide are not limited and may be glucose, sucrose, maltose, galactose, arabinose, ribulose, fructose, rutose, mannose, lactose, cellobiose or mixtures thereof.

The amount of adding the edible thickener is not limited. When the amount of the hydrophilic solvent 4 contained in the capsules is one, the amount of an edible thickener is preferably $1\times10^{-3}$ or more and 10 or less, and is more preferably $1\times10^1$ or more and 1 or less. Within the range of $1\times10^{-3}$ or more, it is possible to increase the viscosity of the hydrophilic solvent 3. Within the range of $1\times10^{-1}$ or more, the effect thereof becomes more remarkable. Within the range of 10 or less, a lowering of the fluidity for the hydrophilic solvent 3 can be restrained, and within the range of 1 or less, the effect thereof becomes more remarkable.

In the present embodiment 1, the weight ratio of the sum of the near-infrared fluorescent dyes, the X-ray contrast mediums and the phospholipids with respect to the hydrophilic solvent (weight ratio of the vesicle and the emulsion) is not limited as far as a sufficient fluorescence intensity can be maintained as a medical tissue-marker and an X-ray CT image are sufficiently captured. Preferably, the weight ratio may be 100:1 or more and 1:100 or less, and more preferably, the weight ratio may be 10:1 or more and 1:1 or less. When the ratio is 100:1 or more, the fluorescence intensity and X-ray absorption ratio of the medical tissue-marker are higher than those of an organ which is background. When the weight ratio is 10:1 or more, the effect thereof becomes remarkable. Furthermore, when the weight ratio is 1:100 or less, the interference is restrained by X-ray absorption with respect to fluorescent light, and when the weight ratio is 1:1 or less, the effect thereof becomes remarkable.

In the present embodiment 1, the weight of the near-infrared fluorescent dyes, the X-ray contrast mediums and the phospholipids which are added into the hydrophilic solvent (weight of the vesicle and the emulsion) is not limited as long as sufficient fluorescence intensity can be maintained as a medical tissue-marker and an X-ray CT image are sufficiently captured. When the weight of the hydrophilic solvent (in the case of including an edible thickener and the like, the weight including the edible thickener, etc.) is one, the weight thereof is preferably $1\times10^{-4}$ or more and $1\times10^{-1}$ or less, and is more preferably $1\times10^{-3}$ or more and $1\times10^{-2}$ or less. Within the range of $1\times10^{-4}$ or more, it is possible to enhance the fluorescence intensity and X-ray absorption ratio, and within the range of $1\times10^{-3}$ or more, the effect thereof becomes more remarkable. Furthermore, within the range of $1\times10^{-1}$ or less, changing into a lamella phase instead of being the vesicle and the emulsion may be restrained in the hydrophilic solvent and within the range of $1\times10^{-2}$ or less, the effect thereof becomes more remarkable.

In the present embodiment 1, the emulsifier is formed on the walls of the capsules in which the hydrophilic solvent is contained, and the emulsifier is used for aggregation as clusters. The emulsifier according to the present embodiment 1 can form not only walls of the capsules but also an epidermis covering entire clusters. Thus, a plurality of capsules can be aggregated and combined. Examples of the emulsifier according to the present embodiment 1 are not limited and may be polyglyceryl polyricinoleate, polyglyceryl polyricinoleate derivative, and glycerol fatty acid ester derivative, or mixtures thereof.

In the present embodiment 1, the weight of the emulsifier added for forming the capsules is not limited. When the weight of the hydrophilic solvent (including the total weight of the near-infrared fluorescent dyes, X-ray contrast mediums and the phospholipids, and in the case where an edible thickener is also included, including the total weight thereof) is one, the weight of the emulsifier is preferably $1\times10^{-3}$ or more and 1 or less, and is more preferably $1\times10^{-2}$ or more and $1\times10^{-1}$ or less. Within the range of $1\times10^{-3}$ or more, the emulsifier can stably make the capsules of the hydrophilic solvent, and within the range of $1\times10^{-2}$ or more, the effect thereof becomes more remarkable. Furthermore, within the range of 1 or less, the reaction in which the emulsifier, hydrophobic solvent and a first hydrophilic solvent form a gel layer is restrained, and within the range of $1\times10^1$ or less, the effect thereof becomes more remarkable.

In the present embodiment 1, the particle diameter is not limited as long as the function for a medical tissue-marker is maintained. For example, the particle diameter is preferably 50 μm or more and 500 μm or less, and is more preferably 100 μm or more and 250 μm or less. Within the range of 50 μm or more, the marker is hard to decompose and the fluorescence intensity for the marker can be enhanced. Within the range of 100 μm or more, the effect thereof becomes more remarkable. Furthermore, within the range of 500 μm or less, it is possible to restrain that an injection needle through an endoscope is stopped. Within the range of 250 μm or less, the effect thereof becomes more remarkable.

In the present embodiment 1, the number of capsules in one cluster is not limited as long as the function for a medical tissue-marker is maintained. For example, the number of capsules is preferably 1 or more and $10^3$ or less, and is more preferably 10 or more and $10^2$ or less. Within the range of 1 or more, the fluorescence intensity is increased and within the range of 10 or more, the effect thereof becomes more remarkable.

Furthermore, within the range of $10^3$ or less, the strength of the capsules is increased and the marker becomes stable, and within the range of $10^2$ or less, the effect thereof becomes more remarkable.

Furthermore, in order to preferably maintain the clusters, a medical tissue-marker according to the present embodiment 1 uses, for example, a hydrophobic solvent, the clusters being maintained in the hydrophobic solvent. Thus, there is an effect that a plurality of capsules are formed and aggregated. Besides the above solvent, in order to stabilize and strengthen the function of the medical tissue-marker, another element such as a hydrophobic polymer and the like can be added to cross-link.

Hereinabove, by a medical tissue-marker according to the present embodiment 1, it is possible to identify a position even in the outside of an organ, to be locally maintained for a long period, and to provide a marking position within an entire organ.

More specifically, a medical tissue-marker according to the present embodiment 1 can strongly and stably generate a near-infrared fluorescent light since near-infrared fluorescent dyes are combined with a vesicle, and can photograph an X-ray CT image since X-ray contrast mediums are forming an emulsion. Furthermore, even when the capsules are contacted with a tissue liquid in a body by being driven into an organ, there is an advantage that each capsule is hard to dissociate and locally to remain for a long period since both the vesicle and the emulsion are incorporated into a hydrophilic solution to form clusters that includes the capsules. There is also the advantage that the strength for a local stay for a long period and flexibility for injection into an organ through passage of an endoscope are maintained since an edible thickener is used for the capsules of the clusters.

(A Method for Manufacturing the Clusters)

Figure 4:
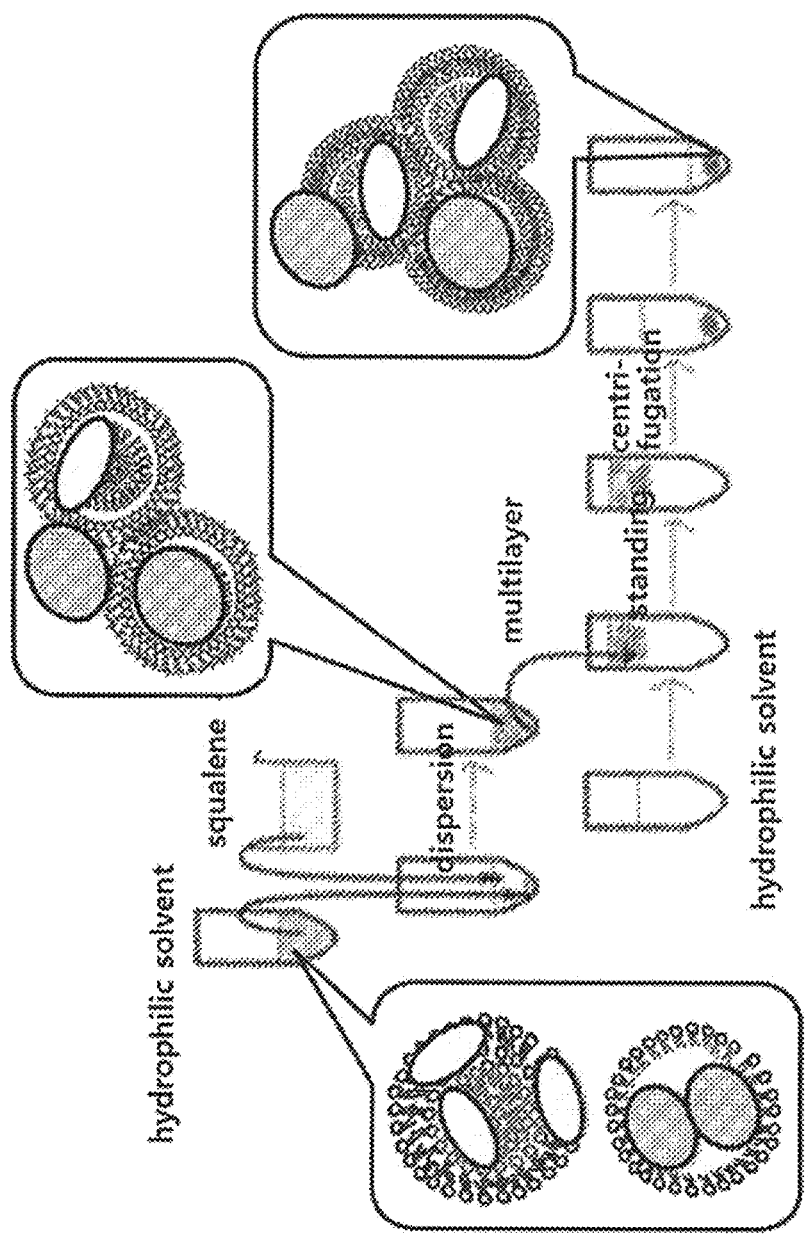
FIG. 4 shows a schematic view for processes of a method for manufacturing clusters according to one embodiment.

Herein, an example of a method for manufacturing a medical tissue-marker (hereinafter, referred to as "the present manufacturing method") is described in detail. FIG. 4 is a schematic view of the present manufacturing method.

As shown in FIG. 4, the present manufacturing method is characterized by comprising a first step of adding a near-infrared fluorescent dye, an X-ray contrast medium and a phospholipid into a first hydrophilic solvent and stirring the first hydrophilic solvent, a second step of adding the first hydrophilic solvent and an emulsifier into a hydrophobic solvent to form a suspension, and a third step of performing centrifugation of the suspension and a second hydrophilic solvent.

By the first step of adding a near-infrared fluorescent dye, an X-ray contrast medium and a phospholipid into a first hydrophilic solvent and stirring the first hydrophilic solvent, a vesicle including the phospholipid combined with the near-infrared fluorescent dye and an emulsion including the phospholipid combined with the X-ray contrast medium can be formed. In the present embodiment 1, there is an advantage that this operation can be performed at one time, and a large device is unnecessary. The step of forming the vesicle and the step of forming the emulsion are separately performed. Then, each solvent may be mixed to be one solvent. In this case, the step of forming the vesicle and the step of forming the emulsion are not limited to the step of adding the phospholipid for stirring. The step of removing the solvent may be performed by a decompression process after the phospholipid is mixed with an organic solvent or supercritical fluid. The step of performing a filter treatment or ultrasonic treatment by adding the phospholipid may also be used. However, from the viewpoints of the enhancement for biocompatibility by not including an organic solvent and stability of the phospholipid, the step of adding the phospholipid for stirring is preferable.

In the first step described above, from the viewpoint of the capsules 4 being easily formed, the first hydrophilic solvent preferably is the same as the hydrophilic solvent which exists in the capsules. That is to say, an example of the first hydrophilic solvent is preferably water, physiological salt water, phosphate buffer solution, TRIS hydrochloric acid buffer solution, HEPES buffer solution, or mixtures thereof.

The first hydrophilic solvent preferably includes an edible thickener. The edible thickener may be gelatin, agar, fibrinogen, a saccharide, or mixtures thereof.

The amount of the near-infrared fluorescent dyes, the X-ray contrast mediums and the phospholipids with respect to the first hydrophilic solvent is not limited. The same range preferably applies in relation to the near-infrared fluorescent dyes, the X-ray contrast mediums and the phospholipids in the hydrophilic solvent which exists in the capsules. That is to say, when the weight (in the case of including an edible thickener and the like, including the weight thereof) of the first hydrophilic solvent is one, the weight thereof is preferably $1\times10^{-4}$ or more and $1\times10^{-1}$ or less, and is more preferably $1\times10^{3}$ or more and $1\times10^{-2}$ or less. Within the range of $1\times10^{-4}$ or more, the intensity of the fluorescent light is increased and an X-ray CT image is sufficiently captured, and within the range of $1\times10^{-3}$ or more, the effect thereof becomes more remarkable. Furthermore, within the range of $1\times10^{-1}$ or less, changing into the lamellar phase instead of vesicles and the emulsion in the hydrophilic solvent is restrained, and within the range of $1\times10^{-2}$ or less, the effect thereof becomes more remarkable.

The temperature for performing the first step is not limited as long as the vesicles and an emulsion can be formed. An example thereof is preferably 4° C. or more and 80° C. or less and, more preferably, room temperature for convenience. The time for stirring the first hydrophilic solvent is also not limited as long as the vesicle and the emulsion can be formed. An example thereof is preferably 5 minutes or more and 1 hour or less, and more preferably is 10 minutes or more and 30 minutes or less.

By the second step for forming the suspension by adding the first hydrophilic solvent and the emulsifier into the hydrophobic solvent, the emulsifier can be boarded on around the first hydrophilic solvent in which the vesicle and the emulsion are incorporated, and a plurality of capsule-shaped emulsions in the hydrophobic solvent can be formed.

The hydrophobic solvent in the second step is not limited as long as the capsule-shaped emulsion is formed at a temperature of 4° C. or more and 80° C. or less. Examples of the hydrophobic solvent are kerosene, hexane, decane, dodecane, heptane, squalene, squalane, liquid paraffin, mineral oil or mixtures thereof.

In the present embodiment 1, the weight of the hydrophobic solvent is not limited. When the weight of the hydrophilic solvent is one, the weight of the hydrophobic solvent is preferably 1 or more and 100 or less, and is more preferably 5 or more and 10 or less. Within the range of 1 or more, it is restrained that capsule-shaped emulsion is transferred to the gel phase, and within the range of 5 or more, the effect thereof becomes more remarkable. Furthermore, within the range of 100 or less, the clusters stably maintain a particle diameter of the capsule-shaped emulsion, and within the range of 10 or less, the effect thereof becomes more remarkable.

In the second step, the emulsifier described above can be employed.

In the second step, the amount of the first hydrophilic solvent can be properly adjusted without limitation. For example, when the weight amount of the hydrophobic solvent is one, the amount of the first hydrophilic solvent is preferably $1\times10^{-3}$ or more and 1 or less, and is more preferably $1\times10^{-2}$ or more and $1\times10^{-1}$ or less. Within the range of $1\times10^{-3}$ or more, the intensity of the fluorescent light of a marker is enhanced by increasing the number of capsules per cluster, and within the range of $1\times10^{-2}$ or more, effect thereof becomes more remarkable. Furthermore, within the range of 1 or less, phase separation between the hydrophilic solvent and the hydrophobic solvent is restrained, and within the range of $1\times10^{-1}$ or less, the effect thereof becomes more remarkable.

In the second step, the amount of the emulsifier can be properly adjusted without limitation. For example, when the weight amount of the hydrophilic solvent is one, the emulsifier is preferably $1\times10^{-3}$ or more and 1 or less, and is more preferably $1\times10^{-2}$ or more and $1\times10^{-1}$ or less. Within the range of $1\times10^{-3}$ or more, the emulsifier stably generates the capsules of the hydrophilic solvent, and within the range of $1\times10^{-2}$ or more, the effect thereof becomes more remarkable. Furthermore, within the range of 1 or less, the reaction in which the emulsifier, the hydrophobic solvent and the first hydrophilic solvent form a gel layer is restrained, and within the range of $1\times10^{-1}$ or less, the effect thereof becomes more remarkable.

Figure 5:
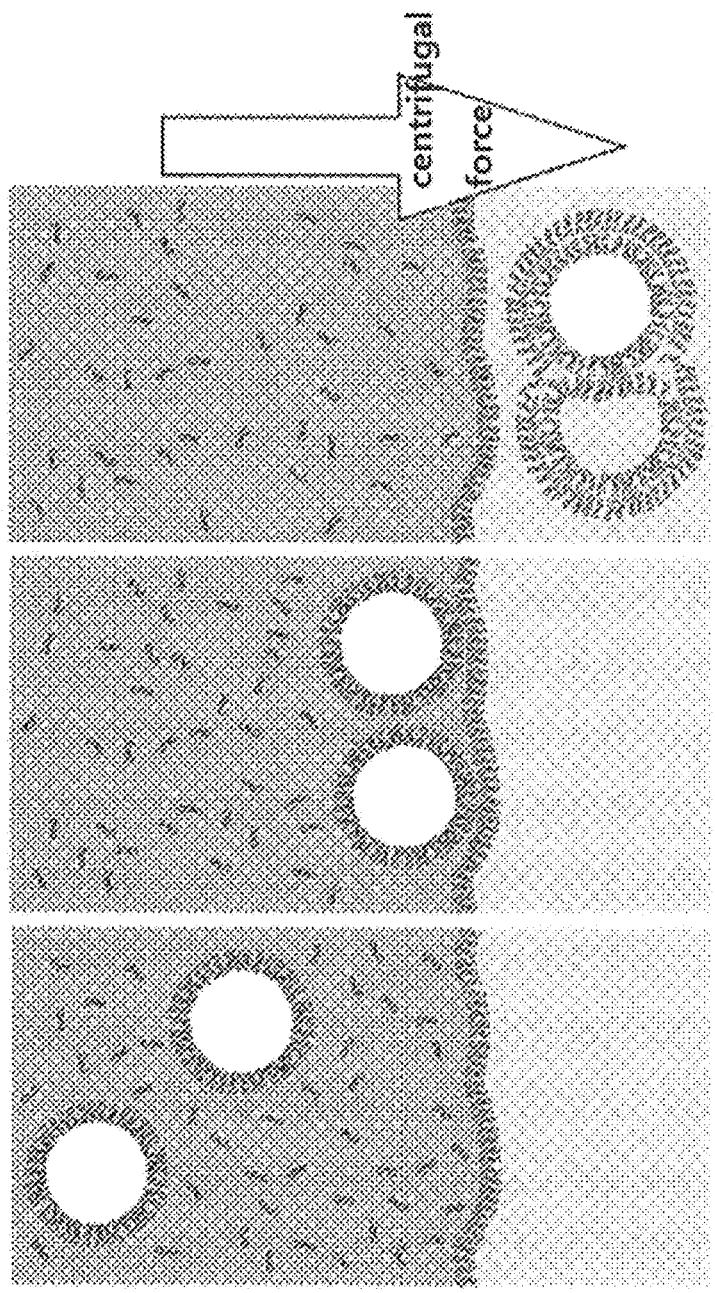
FIG. 5 shows a drawing that displays processes for manufacturing clusters according to one embodiment.

In the present embodiment 1, the third step of performing centrifugation by the suspension and a second hydrophilic solvent is a method in which a hydrophobic solvent layer and a hydrophilic solvent layer is phase-separated for an arrangement and the capsule-shaped emulsion existing in the hydrophobic solvent is precipitated in the hydrophilic solvent by centrifugation. In FIG. 5, the schematic view is shown. As a result, the emulsion on the interface between the hydrophobic solvent layer and the hydrophilic solvent layer can form clusters from the capsules.

A second hydrophilic solvent may be used for centrifugation without limitation. For example, water, physiological salt water, phosphate buffer solution, TRIS hydrochloric acid buffer solution, HEPES buffer solution, or mixtures thereof is preferably used.

The amount of a second solvent is not limited. For example, when the amount of suspension is one, the second solvent is preferably 1 or more and 1000 or less, and more preferably 10 or more and 100 or less. Within the range of 1 or more, phase separation between the hydrophobic solvent layer and the hydrophilic solvent layer can be stabilized, and within the range of 10 or more, the effect thereof becomes more remarkable. Furthermore, within the range of 1000 or less, the lowering of the viscosity can be restrained, and within the range of 100 or less, the effect thereof becomes more remarkable.

As a result, a medical tissue-marker can be configured.

Embodiment 2

(A Medical Tissue-Marker)

A medical tissue-marker according to the present embodiment 2 is almost the same as the embodiment 1 except that when the suspension is formed by adding a first hydrophilic solvent and an emulsifier to a hydrophobic solvent, an X-ray contrast medium is added into the hydrophobic solvent. The difference therebetween is described below.

Figure 6:
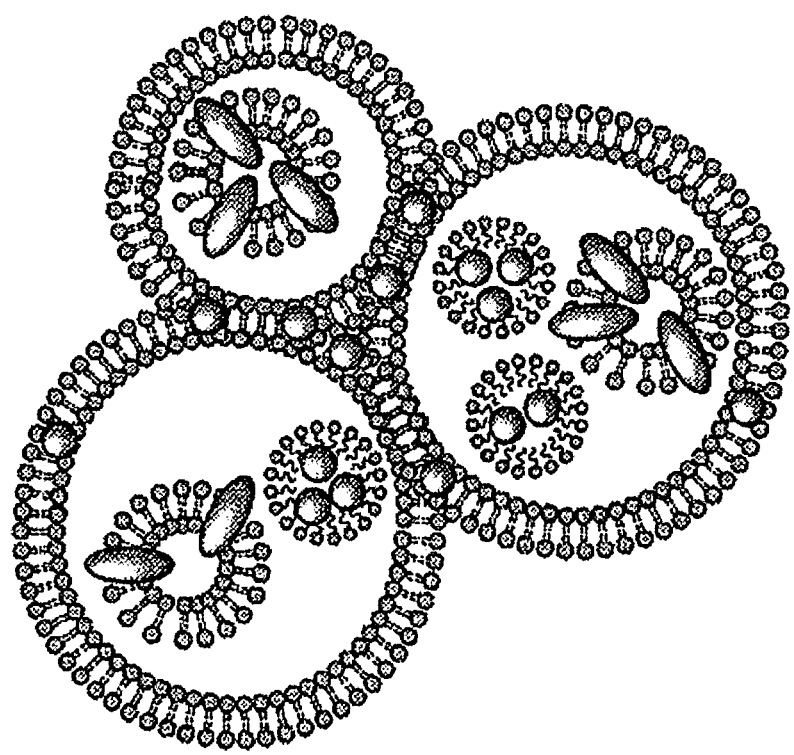
FIG. 6 shows a schematic view of clusters according to one embodiment.

FIG. 6 is a schematic view for the clusters 1 in a medical tissue-marker according to the present embodiment 2. As shown in FIG. 6, a medical tissue-marker according to the present embodiment 2 is characterized by including the X-ray contrast medium, even in the outside of the capsules 5. Thus, lots of the X-ray contrast medium can be included. It is also possible to include the X-ray contrast medium located in near distance with the outside of the clusters 1. Thus, the sensitivity thereof is enhanced.

(A Method for Manufacturing Clusters)

Herein, a method for manufacturing a medical tissue-marker according to the present embodiment 2 is described. A method for manufacturing clusters according to the present embodiment 2 is almost the same as the embodiment 1 except that the suspension is formed by adding a first hydrophilic solvent and an emulsion into a hydrophobic solvent in the second step of the embodiment 1. Specifically, when the suspension is formed by adding the first hydrophilic solvent and the emulsifier into the hydrophobic solvent, adding an X-ray contrast medium differs from the embodiment 1.

The X-ray contrast medium added in the second step is the same as in the embodiment 1. The concentration of the X-ray contrast medium is not specially limited. For example, when the amount of the first hydrophilic solvent is one, the amount of the X-ray contrast medium is preferably 0.01 or more and 10 or less, and more preferably 0.1 or more and 1 or less. Within the range of 0.01 or more, the sensitivity for the X-ray contrast image is increasing, and within the range of 0.1 or more, the effect thereof becomes more remarkable. Furthermore, within the range of 10 or less, when the clusters are fabricated, precipitation due to its weight is restrained, and within the range of 1 or less, the effect thereof becomes more remarkable.

Hereinabove, by a medical tissue-marker according to the present embodiment 2, it is possible to identify a position from the outside of an organ, even when marked on the inside of an organ, and to be locally stable for a long period. It is also possible to provide a marking position within an entire organ. Especially, by a marker according to the present embodiment 2, the X-ray contrast medium can be included, even in the outside of the capsules. Thus, the sensitivity thereof is increased.

EXAMPLES

Herein, a medical tissue-marker was specifically fabricated and the effects of the present invention were confirmed. Hereinafter, the details are described below.

Example 1

In the present example 1, TRIS hydrochloric acid buffer solution as a first hydrophilic solvent, indocyanine green (hereinafter, referred to as "ICG") as a near-infrared fluorescent dye, iodized poppy oil ethyl ester (hereinafter, referred to as "LPD") as a X-ray contrast medium, and egg yolk lecithin as a phospholipid were employed, respectively. Sucrose as a thickener was also employed.

TRIS buffer solution of 1 mL was prepared to be 50 mM and pH 7.8 in a glass tube at room temperature. Then, ICG of $2\times10^{-2}$ mM, LPD of 20 mM, and egg yolk lecithin of 30 mM were added thereto for stirring. A vesicle and an emulsion were formed.

Then, polyglyceryl polyricinoleate (PGPR) of 15 w/w % was dissolved into squalene of a hydrophobic solvent of 15 mL. The solution of 1 mL including the vesicle and the emulsion fabricated was added thereto. A suspension including the emulsion by PGPR (PGPR emulsion) was prepared. In the present example 1, LPD of 4 mM was added even into the hydrophobic solvent. Thus, the LPD existed in the PGPR emulsion or surrounding the PGPR emulsion.

Then, TRIS buffer solution of 5 mL having 50 mM and pH7.7 was prepared as a second hydrophilic solution. A suspension of 10 mL including the PGPR emulsion was added into the second hydrophilic solution from the upper side by using glucose as a thickener. An oil phase (squalene phase) and aqueous phase (TRIS buffer solution phase) were contacted each other and rotated at a speed of 3500 rpm for 30 minutes at room temperature to form clusters of PGPR.

Figure 7:
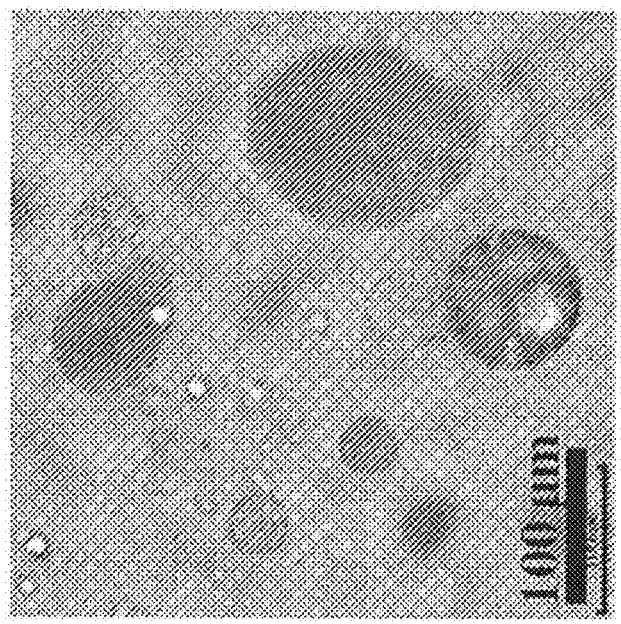
FIG. 7 shows a bright-field microscopic image of clusters according to an example.
Figure 8:
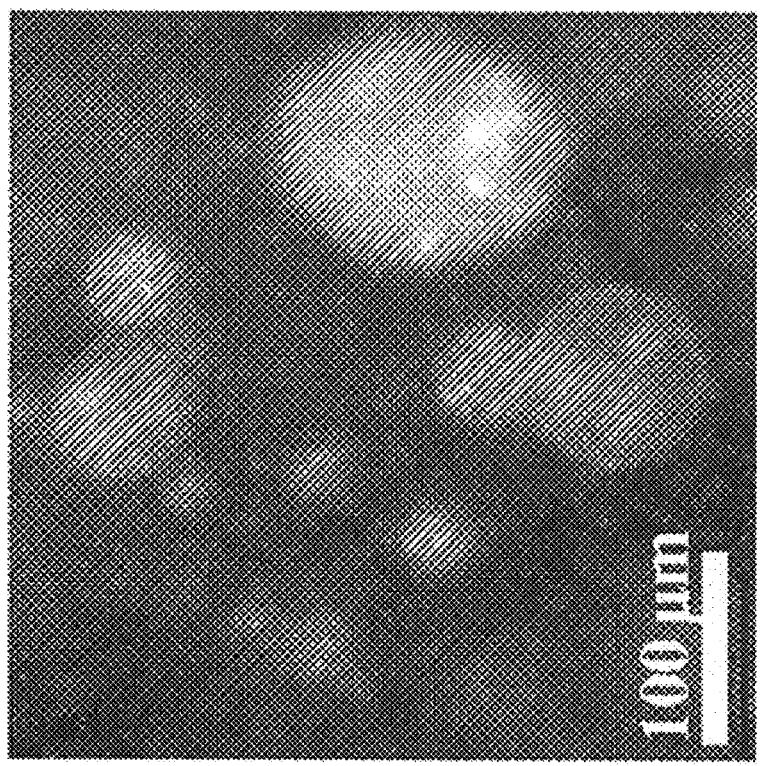
FIG. 8 shows a fluorescent microscopic image of clusters according to an example.
Figure 9:
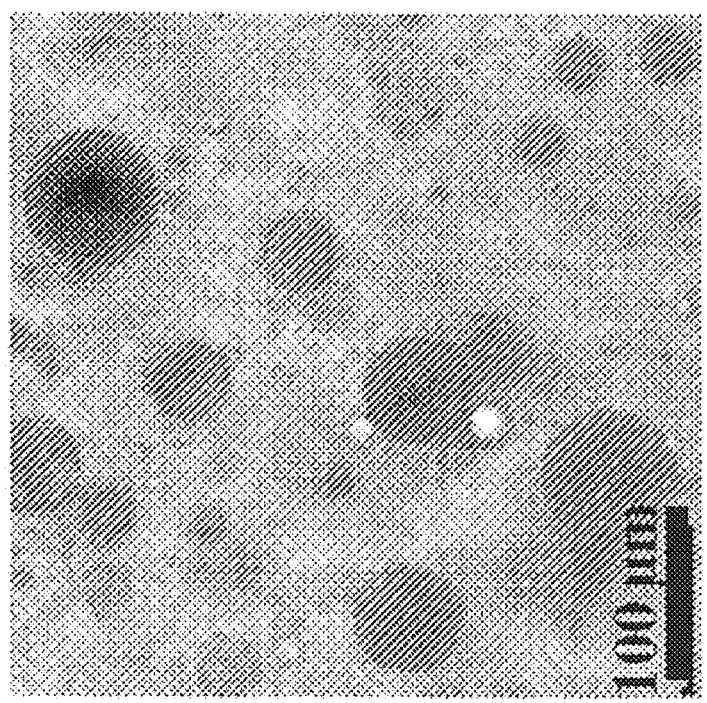
FIG. 9 shows a bright-field microscopic image (after 27 hours) of clusters according to an example.
Figure 10:
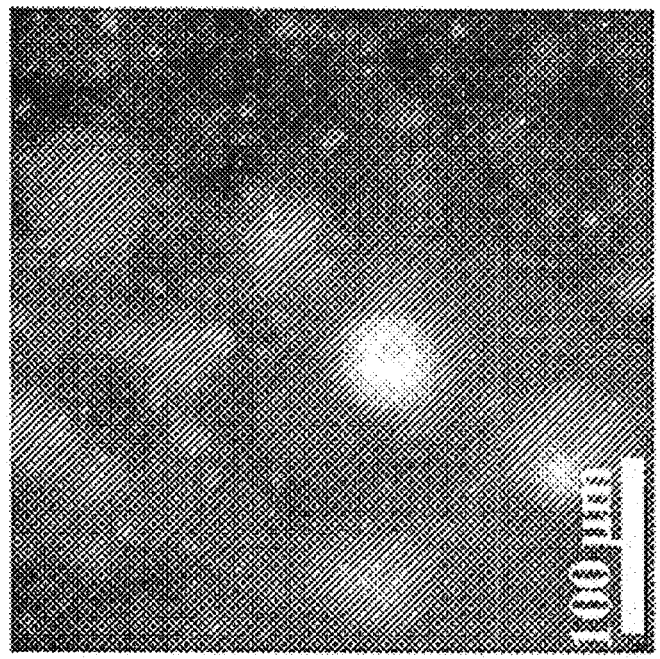
FIG. 10 shows a fluorescent microscopic image (after 27 hours) of clusters according to an example.

FIG. 7 is a bright-field microscopic image of clusters of PGPR. FIG. 8 is a fluorescent microscopic image. From FIG. 7 and FIG. 8, existing clusters and generation of fluorescent light were confirmed. FIG. 9 is a bright-field microscopic image when clusters of PGPR were fabricated and 27 hours had passed. FIG. 10 is a fluorescent microscopic image when clusters of PGPR were fabricated and 27 hours had passed. As a result, even after one day or more passed, it was confirmed that the shape and function of the clusters were stable.

Figure 11:
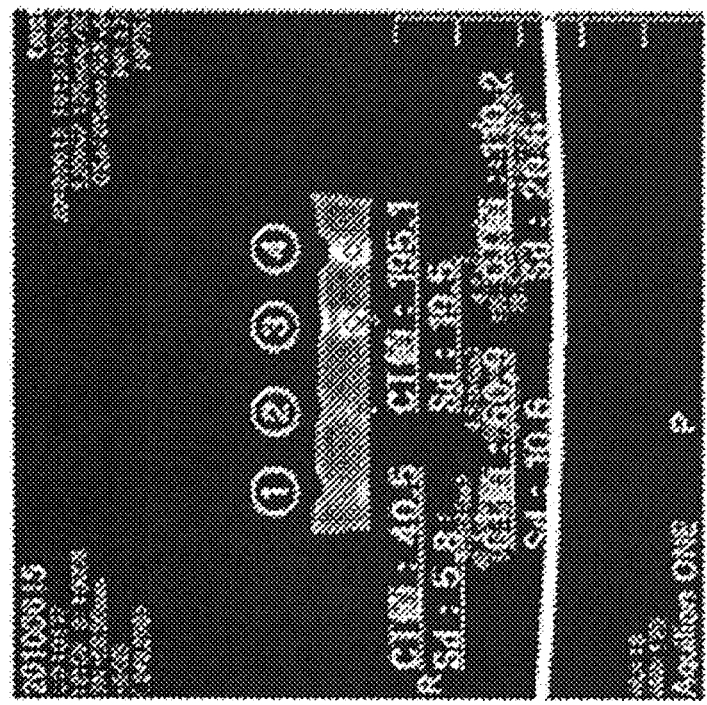
FIG. 11 shows a result for an X-ray CT image of clusters according to an example.

FIG. 11 shows a result of an X-ray computed tomography (CT) in a state of fluid dispersion with respect to the clusters. From FIG. 11, it was confirmed that the X-ray absorption (CT numbers) of the clusters were sufficiently higher than that of the stomach wall itself.

Figure 12:
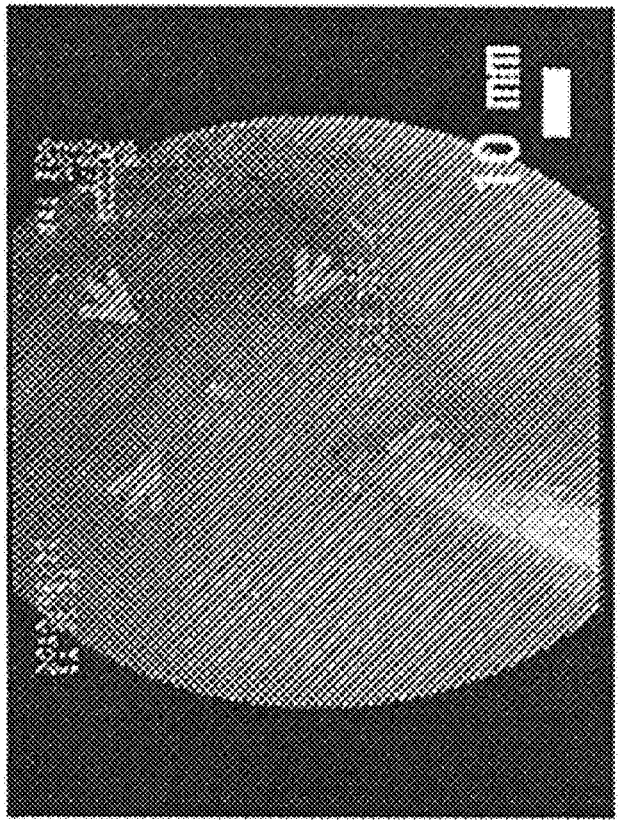
FIG. 12 shows an endoscopic view of the inside of the stomach wall of a pig when clusters are injected according to an example.
Figure 13:
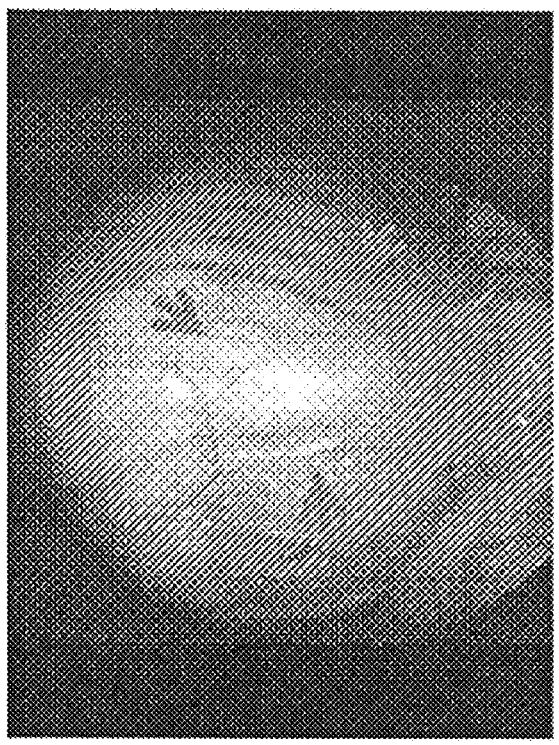
FIG. 13 shows a laparoscopic view of the outside of the stomach of a pig when clusters are injected according to an example.

Then, the fabricated clusters were injected into biological tissue and the result thereof was confirmed. Specifically, submucosal layer of the stomach wall of a pig was a most suitable target of the marker administration. The fluid dispersion of 300 μl, including the clusters, was administrated on four points surrounding a metal clip placed inside the stomach by local injection. FIG. 12 shows an endoscopic view of the inside of the stomach. FIG. 13 shows a laparoscopic view of the outside of the stomach.

Figure 14:
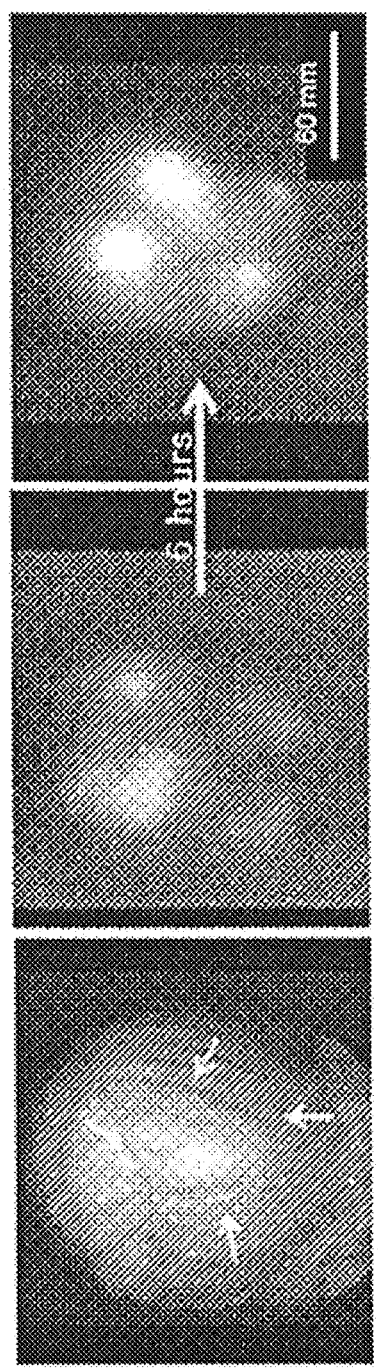
FIG. 14 shows fluorescent laparoscopic images of the outside of the stomach of a pig when clusters are injected according to an example.
Figure 15:
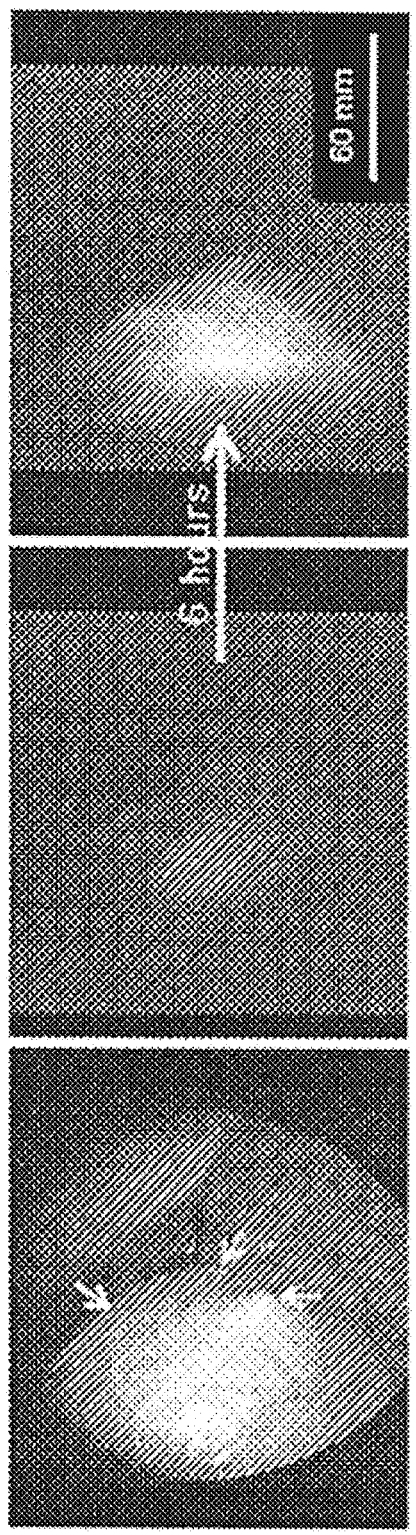
FIG. 15 shows fluorescent laparoscopic images of the outside of the stomach of a pig when an ICG aqueous solution is injected according to an example.

FIG. 14 shows fluorescent images of the outside of the stomach. The left and middle panels show conventional and fluorescent laparoscopic images immediately after local injection, respectively. The right panel showed a fluorescent image 6 hours after injection. As shown in FIG. 14, even after 6 hours, four injection points were clearly identified. It was confirmed that the clusters were sufficiently stable at the injection points. FIG. 15 shows the fluorescent images when an ICG aqueous solution was locally injected at the positions similar to those as indicated in FIG. 14. In this case, the exact injection positions were unclear immediately after injection as well as 6 hours after injection.

Figure 16:
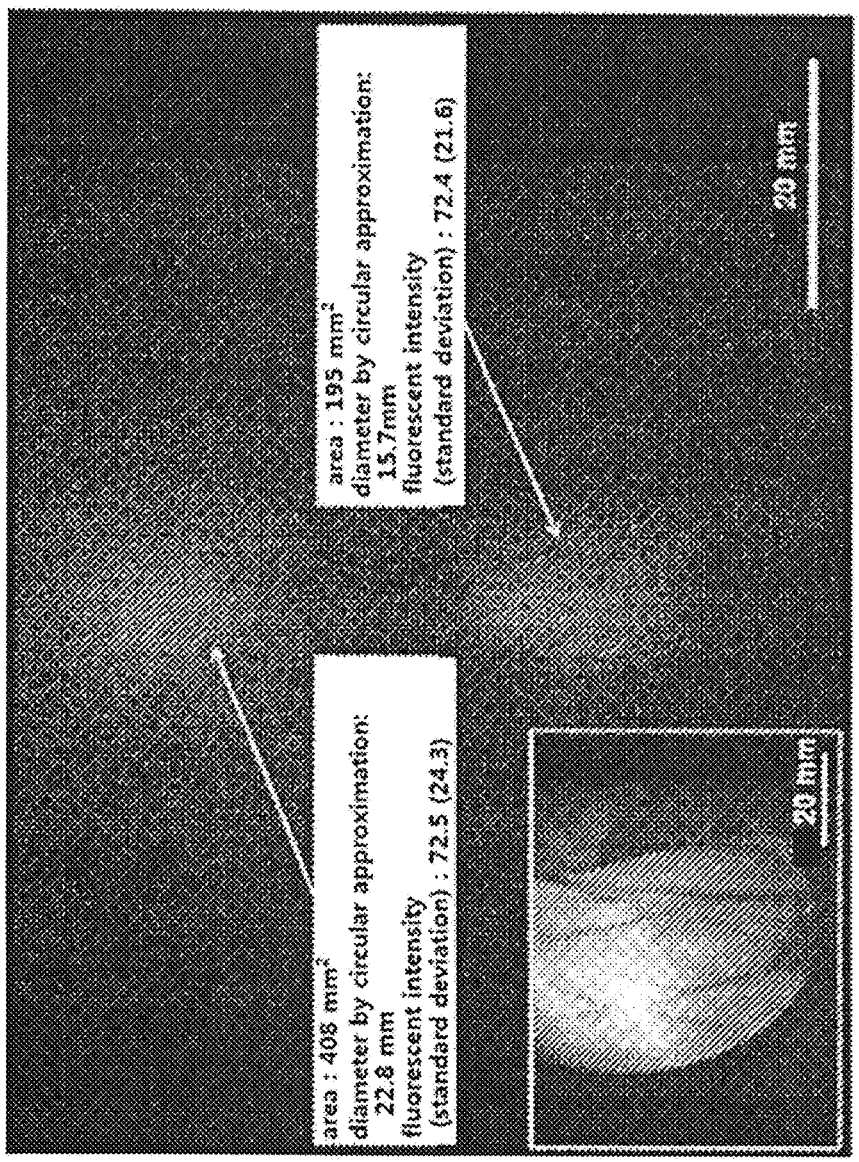
FIG. 16 shows fluorescent laparoscopic images of the outside of the stomach of a pig when clusters are injected (after 24 hours) according to an example.

Herein, the stability was again confirmed 24 hours after the local injection of the marker. The submucosal layer of the stomach wall was a most suitable target of the marker administration. The fluid dispersion of 300 μl including clusters was administrated at two points surrounding a metal clip by local injection. The pig recovered from general anesthesia after the administration. Twenty-four hours later, laparoscopy was performed again under general anesthesia. A fluorescent laparoscope view of the outside of the stomach revealed sufficient fluorescent intensity at the injection points as indicated in FIG. 16.

Figure 17:
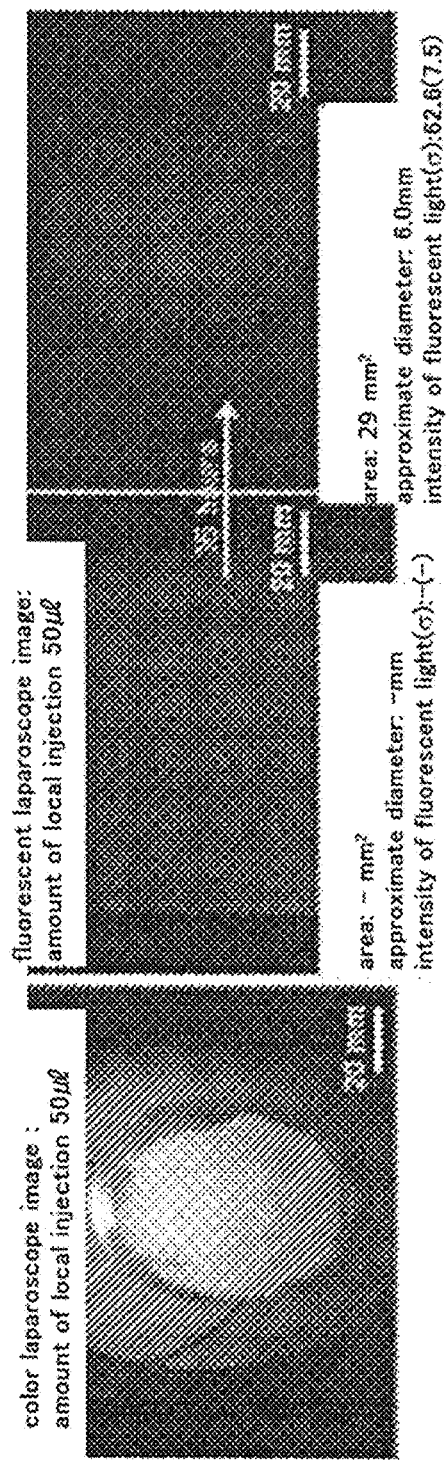
FIG. 17 shows fluorescent images when the amount of an injection is 50 μl according to an example.
Figure 18:
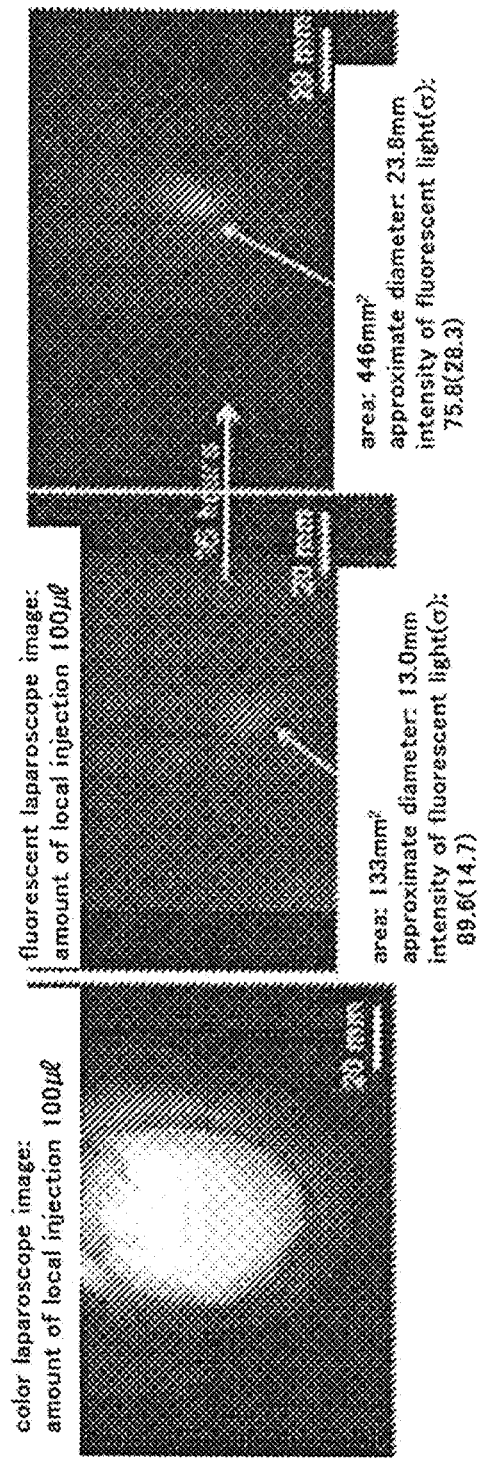
FIG. 18 shows fluorescent images when the amount of an injection is 100 μl according to an example.
Figure 19:
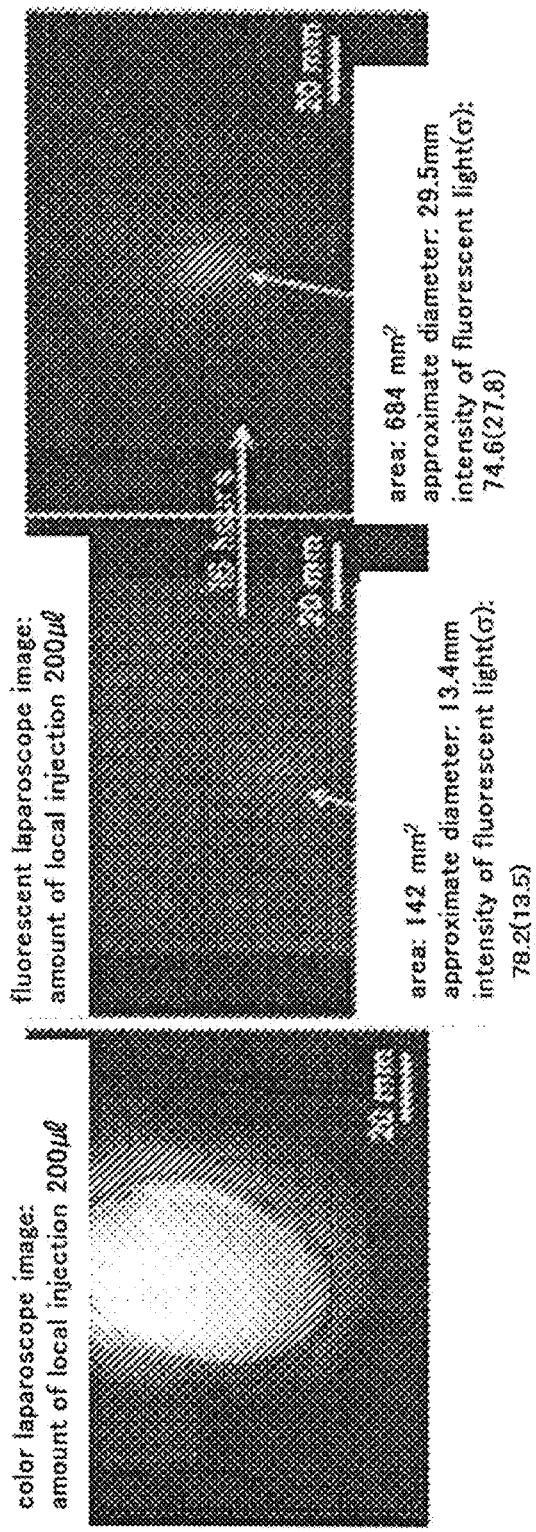
FIG. 19 shows fluorescent images when the amount of an injection is 200 μl according to an example.
Figure 20:
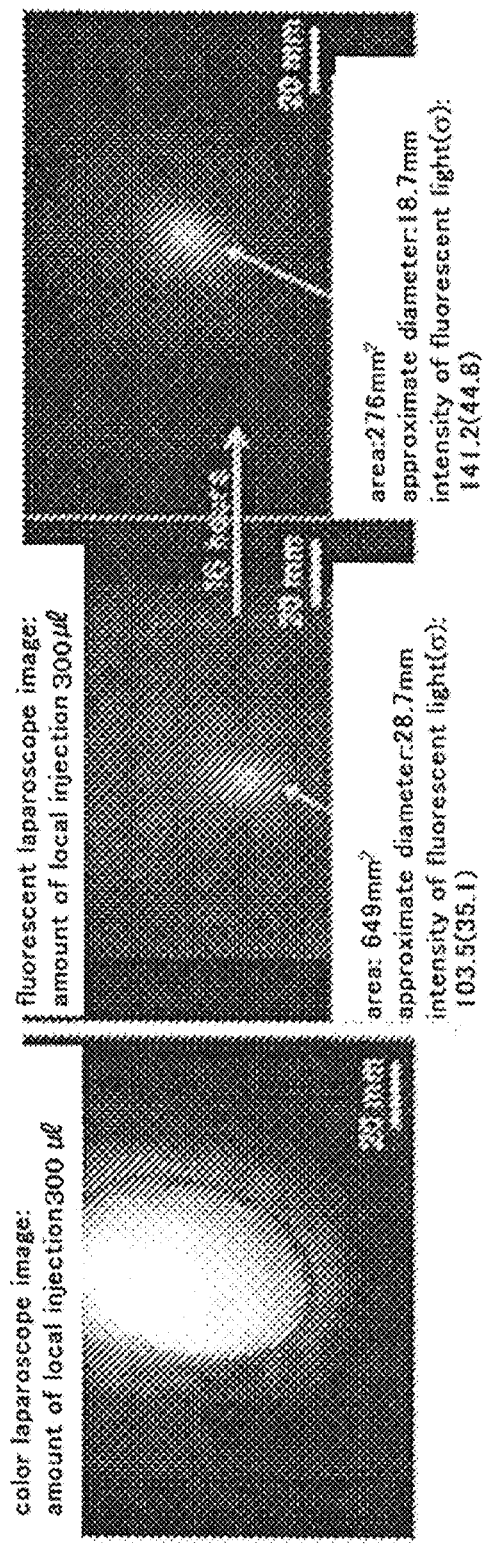
FIG. 20 shows fluorescent images when the amount of an injection is 300 μl according to an example.

The optimum injection amount of the marker was verified. When the concentration of the clusters according to the example 1 was 100 μl or more, the injection points could be confirmed. The concentration thereof was preferably 200 μl or more, and is more preferably 300 μl or more. The fluorescent images of the injection site with various amounts of the marker are shown in FIGS. 17 to 20. In FIG. 17, 50 μl was used. In FIG. 18, 100 μl was used. In FIG. 19, 200 μl was used. In FIG. 20, 300 μl was used.

Figure 21:
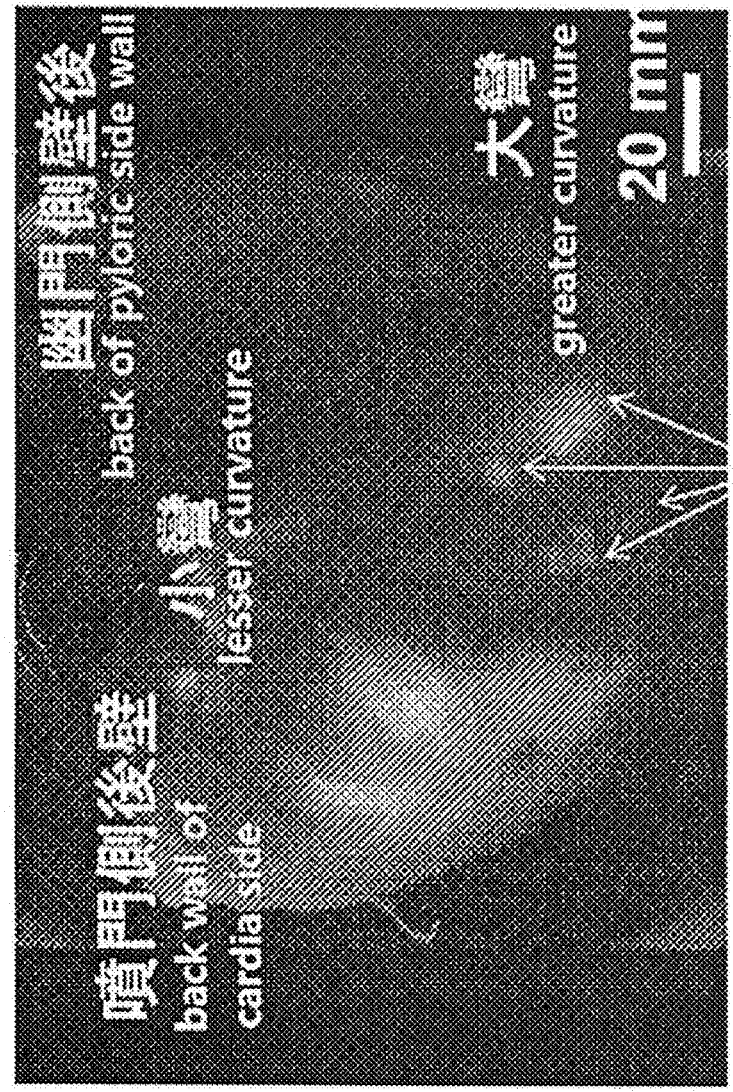
FIG. 21 is a fluorescent image of the excised stomach 32 hours after the administration of clusters according to an example.

Then, the stomach of the pig was excised, and fluorescence and X-ray CT imaging was performed 32 hours after the marker (300 μl each at four points around a metal clip) administration. The fluorescence imaging with the use of a near-infrared LED light showed four spots of individually distinguishable fluorescence on the marker injection site (pyloric side of the stomach, i.e., right side on the image of the stomach, in FIG. 21) and broad diffusion of the fluorescence on the site of ICG aqueous solution injection site (cardia side of the stomach, i.e., left side on the image of the stomach, in FIG. 21.)

Figure 22:
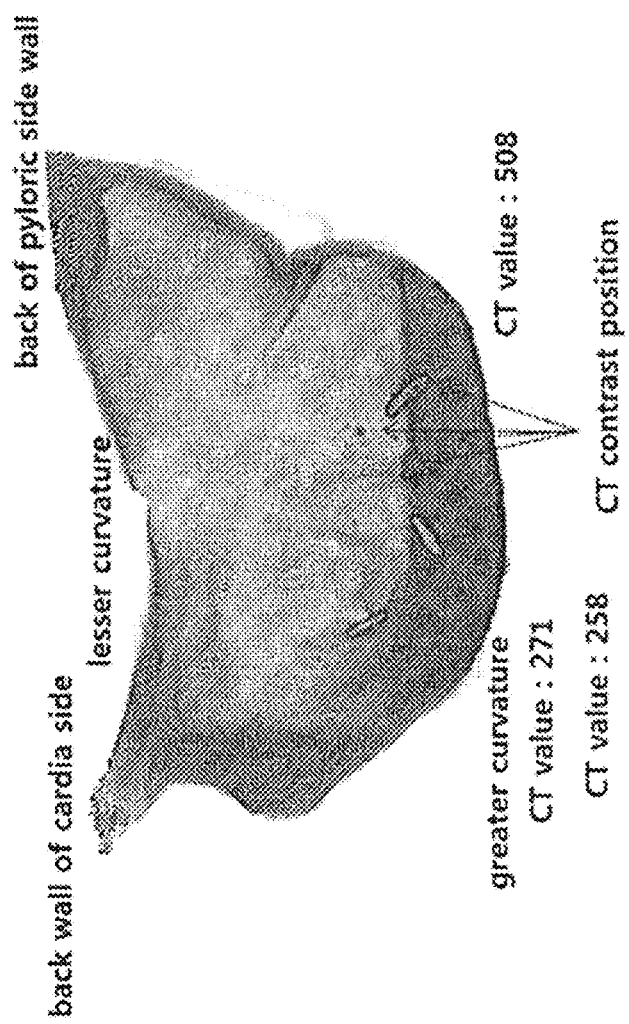
FIG. 22 is an X-ray CT image of the excised stomach 32 hours after the administration of clusters according to an example.

Furthermore, a volumetric reconstruction of the X-ray CT images of the stomach was performed to allow three-dimensional analysis of the location of the injection sites. FIG. 22 shows the three-dimensional reconstructed CT images. The injection sites of the marker on the three-dimensional image were observed in exactly the same location with that revealed under the fluorescent laparoscope observation.

Hereinabove, according to the example 1, it was confirmed that a medical tissue-marker and a manufacturing method therefor were provided. This medical tissue-marker could be detected by X-ray CT as well as fluorescent imaging. Furthermore, the injection site of the marker could be identified from the outside of an organ, and to be locally stable for a long period, and it is easy to provide a marking location within the entire organ.

Figure 23:
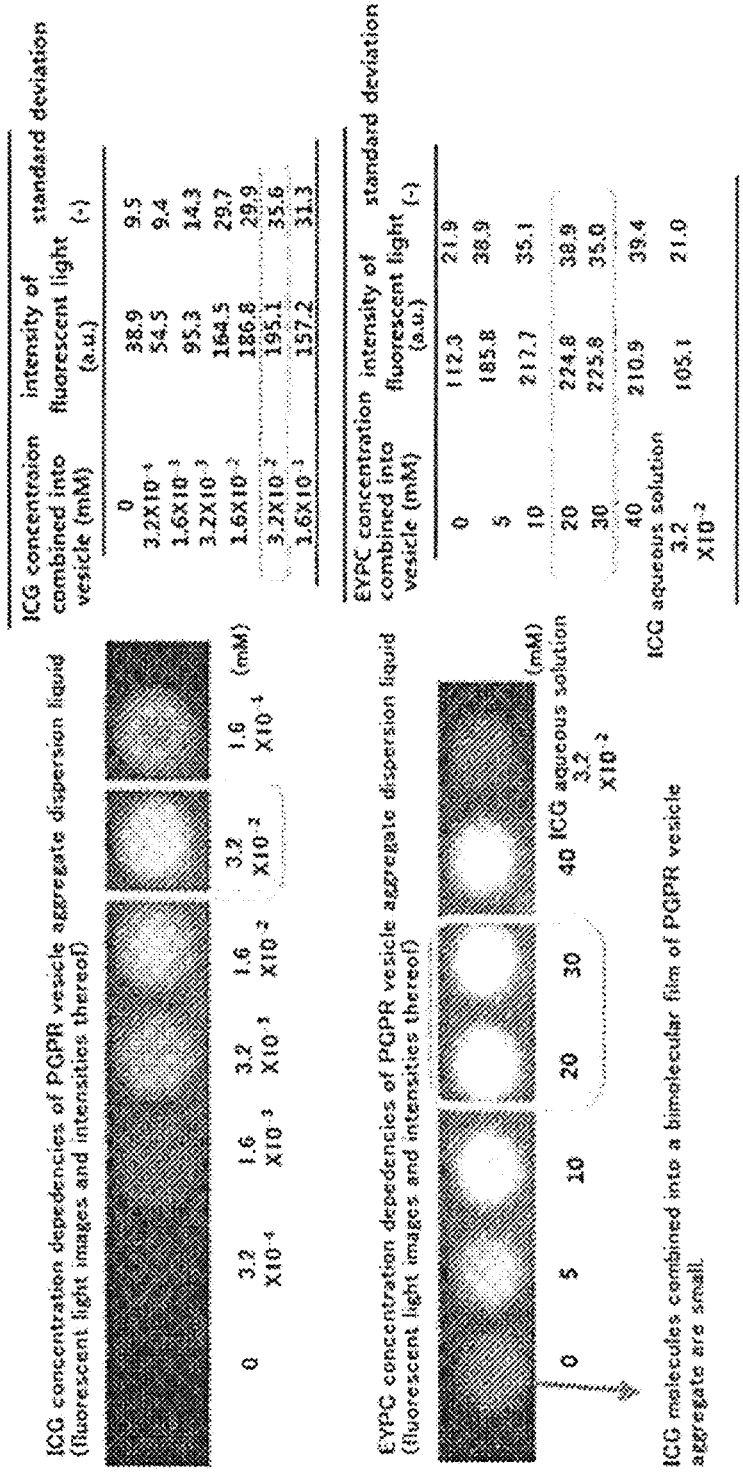
FIG. 23 shows images in which intensities of fluorescence are varied when the ICG concentration and egg yolk lecithin concentration are changed.

In the example 1, for example, the concentration of ICG was $3.2 \times 10^{-2}$ mM and the concentration of ICG can be adjustable. In FIG. 23($a$), changes of fluorescence intensity are shown when the concentration of ICG combined with the vesicle was varied (egg yolk lecithin of 30 mM). In FIG. 23($b$), changes of fluorescence intensity are shown when the concentration of egg yolk lecithin combined with the vesicle was varied (the concentration of ICG aqueous solution of $3.2 \times 10^{-2}$ mM). It was confirmed that the concentration of ICG was preferably $3.2 \times 10^{-1}$ mM or more and $1.6 \times 10^{-1}$ mM or less, and the concentration of egg yolk lecithin was 5 mM or more and 40 mM or less.

Example 2

In the present example 2, a medical tissue-marker was fabricated by using the same material and method used in the example 1 except that LPD was only added to a first hydrophilic solvent. The difference therebetween is mainly described below.

A TRIS buffer solution of 1 mL was prepared to be 50 mM and pH 7.8 in a glass tube at room temperature. Then, ICG of $3.2 \times 10^{-2}$ mM, LPD of 20 mM, egg yolk lecithin of 30 mM were added thereto for stirring. A vesicle and an emulsion were formed.

Then, polyglyceryl polyricinoleate (PGPR) of the emulsifier having 15 w/w % was dissolved into squalene of a hydrophobic solvent of 15 mL. The solution of 1 mL including the vesicle and the emulsion fabricated was added thereto. A suspension including the emulsion by PGPR (PGPR emulsion) was prepared. In the present example 2, no LPD was added into the hydrophobic solvent.

Then, a TRIS buffer solution of 5 mL having 50 mM and pH7.7 was prepared as a second hydrophilic solution. A suspension of 10 mL including the PGPR emulsion was added into the second hydrophilic solution from the upper side by using glucose as a thickener. An oil phase (squalene phase) and aqueous phase (TRIS buffer solution phase) were contacted each other and rotated at a speed of 3500 rpm for 30 minutes at room temperature to form clusters of PGPR.

Figure 24:
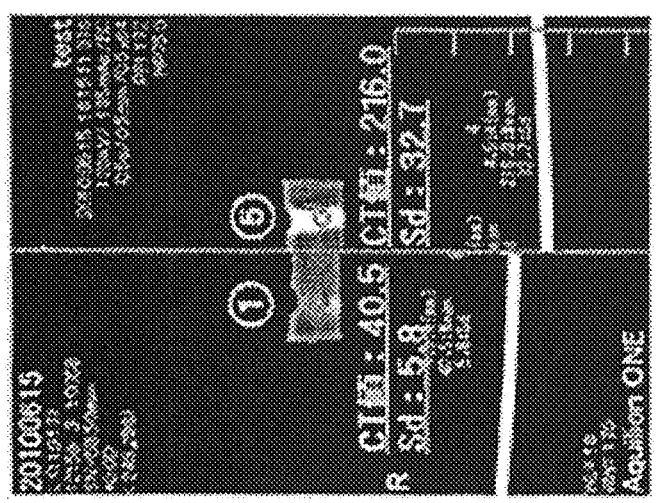
FIG. 24 shows X-ray CT images when the vesicle fabricated in example 2 is dispersed in a liquid.

FIG. 24 shows X-ray CT images of clusters fabricated in a fluid dispersion. Even in clusters, the X-ray absorption (CT numbers) of it is sufficiently higher than that of the stomach wall itself.

Example 3

In the present example 3, a medical tissue-marker using ICG-8 shown in chemical formula (5) of ICG derivative was fabricated in the following steps. A TRIS buffer solution of 1 mL was prepared to be 50 mM and pH 7.8 in a glass tube at room temperature. Then, ICG-8 of $3.2 \times 10^2$ mM, LPD of 40 mg/mL, egg yolk lecithin of 30 mM were added thereto for stirring. A vesicle and an emulsion were formed.

[chemical formula 5]

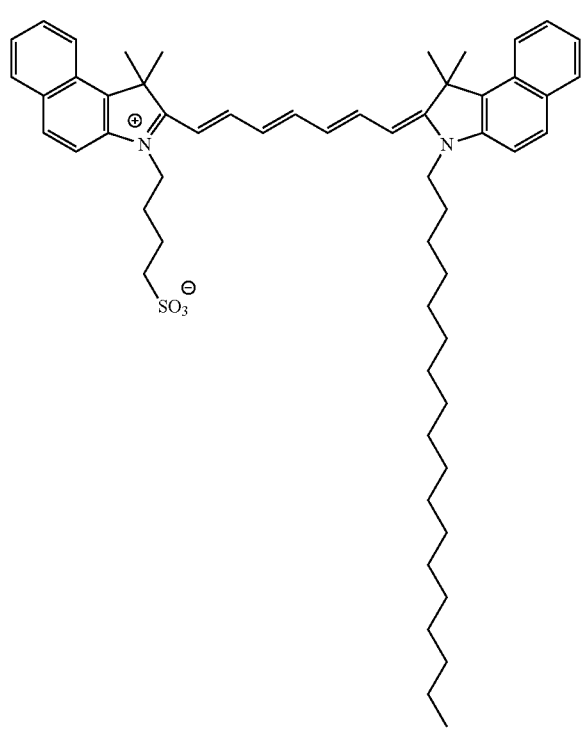

(5)

Then, polyglyceryl polyricinoleate (PGPR) of the emulsifier having 15 w/w % and LPD of 160 mg/mL were dissolved into squalene of a hydrophobic solvent of 15 mL. The solution of 1 mL including the vesicle and the emulsion fabricated was added thereto. A suspension including an emulsion by PGPR (PGPR emulsion) was prepared.

Then, a TRIS buffer solution of 5 mL having 50 mM and pH7.7 was prepared as a second hydrophilic solution. A suspension of 10 mL including the PGPR emulsion and LPD were added into the second hydrophilic solution from the upper side by using glucose as a thickener. An oil phase (squalene phase) and aqueous phase (TRIS buffer solution phase) were contacted each other and rotated at a speed of 3500 rpm for 30 minutes at room temperature to form clusters of PGPR.

Figure 25:
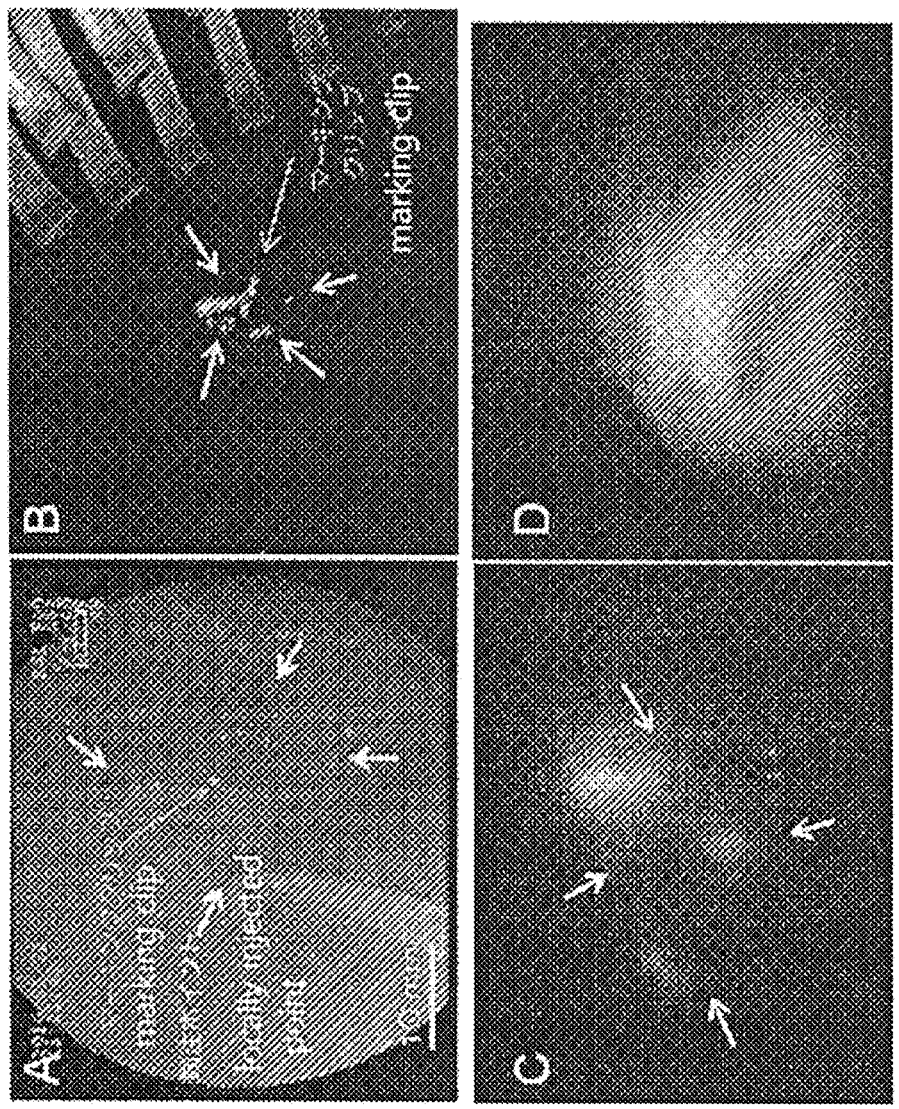
FIG. 25 shows the endoscopic view of the local injection of clusters fabricated in example 3 into the submucosal layer of the stomach wall (A), a three-dimensional volumetric reconstruction of X-ray CT images immediately after the administration of the marker (B), a fluorescence laparoscopic view from the outside of the stomach 18 hours after administration of the marker (C), and a fluorescence laparoscopic view from the outside of the stomach 18 hours after administration of ICG aqueous solution.

FIG. 25 shows the results that (A) the present medical tissue-marker was injected with every 300 μl into four points on a circumference of a circle for a submucosal layer of the stomach wall of a pig under general anesthesia, (B) it was possible to clearly identify the four points of the injection in three-dimensional reconstruction images of X-ray CT immediately after the administration, (C) the medical tissue-marker locally injected at four points closely located with each other on the stomach wall of the pig were individually distinguishable by fluorescent laparoscope, even 18 hours after administration, and (D) it was impossible to distinguish the four points of locally injected ICG aqueous solution in the same manner as the medical tissue-marker because of broad blurring of the solution through tissues.

Thus, according to the present examples, it was confirmed that a medical tissue-marker and a manufacturing method therefor were provided. With the use of the medical tissue-marker and the manufacturing method therefor, it was possible to obtain marking point images with X-ray CT as well as a fluorescent endoscope, it was also possible to identify the marking positions from the outside of the organ even when administered inside in an organ and to be locally stable for a long period, and it is easy to provide accurate marking positions within an entire organ.

INDUSTRIAL APPLICABILITY

The present invention is industrially applicable to a medical tissue-marker and a manufacturing method therefor.

What is claimed is:

1. A medical tissue-marker comprising:
a plurality of capsules formed and aggregated by an emulsifier, each capsule containing a hydrophilic solvent, a vesicle and an emulsion,
wherein the vesicle is formed by combining a phospholipid and a near-infrared fluorescent dye, the emulsion is formed by combining the phospholipid and an X-ray contrast medium, the X-ray contrast medium is also provided outside of the capsules, the phospholipid is phosphatidylcholine and the X-ray contrast medium is a member selected from the group consisting of iodobenzene and derivatives thereof and barium salt and mixtures thereof.

2. The medical tissue-marker according to claim 1, wherein the hydrophilic solvent includes water and an edible thickener.

* * * * *